US00PP26439P2

(12) United States Plant Patent
Misato

(10) Patent No.: US PP26,439 P2
(45) Date of Patent: Mar. 1, 2016

(54) ***VERBENA* PLANT NAMED 'SUNMARIAPRI'**

(50) Latin Name: *Verbena×hybrida*
Varietal Denomination: Sunmariapri

(71) Applicant: Tomoya Misato, Shiga (JP)

(72) Inventor: Tomoya Misato, Shiga (JP)

(73) Assignee: Suntory Flowers LTD., Tokyo (JP)

( * ) Notice: Subject to any disclaimer, the term of this patent is extended or adjusted under 35 U.S.C. 154(b) by 228 days.

(21) Appl. No.: 13/998,607

(22) Filed: Nov. 15, 2013

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Anne Grunberg
(74) *Attorney, Agent, or Firm* — C. A. Whealy

(57) ABSTRACT

A new and distinct cultivar of *Verbena* plant named 'Sunmariapri', characterized by its compact, semi-upright, mounding to cascading plant habit; vigorous growth habit; freely branching habit; early and freely flowering habit; long flowering period; apricot pink-colored flowers that gradually fade to a lighter pink color; and good garden performance.

1 Drawing Sheet

Botanical designation: *Verbena×hybrida.*
Cultivar denomination: 'SUNMARIAPRI'.

BACKGROUND OF THE INVENTION

The present invention relates to a new and distinct cultivar of *Verbena* plant, botanically known as *Verbena×hybrida*, and hereinafter referred to by the name 'Sunmariapri'.

The new *Verbena* plant is a naturally-occurring branch mutation of a proprietary selection of *Verbena×hybrida* identified as code number 1800M, not patented. The new *Verbena* plant was discovered and selected by the Inventor on a single flowering plant of the parent selection in a controlled greenhouse environment in Higashiomi, Shiga, Japan in July, 2011.

Asexual reproduction of the new *Verbena* plant by terminal cuttings in a controlled environment in Higashiomi, Shiga, Japan since July, 2011 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunmariapri'. These characteristics in combination distinguish 'Sunmariapri' as a new and distinct *Verbena* plant:

1. Compact, semi-upright, mounding to cascading plant habit.
2. Vigorous growth habit.
3. Freely branching habit.
4. Early and freely flowering habit.
5. Long flowering period.
6. Apricot pink-colored flowers that gradually fade to a lighter pink color.
7. Good garden performance.

Plants of the new *Verbena* can be compared to plants of the parent selection. Plants of the new *Verbena* differ primarily from plants of the parent selection in flower color as plants of the parent selection have light pale pink and red purple bicolored flowers.

Plants of the new *Verbena* can be compared to plants of *Verbena* 'Sunmaripeach', not patented. In side-by-side comparisons conducted in Higashiomi, Shiga, Japan, plants of the new *Verbena* differed primarily from plants of 'Sunmaripeach' in the following characteristics:

1. Plants of the new *Verbena* were larger than plants of 'Sunmaripeach'.
2. Plants of the new *Verbena* had shorter internodes than plants of 'Sunmaripeach'.
3. Leaves of plants of the new *Verbena* were ovate in shape whereas leaves of plants of 'Sunmaripeach' were trullate in shape.
4. Plants of the new *Verbena* had smaller inflorescences and smaller flowers than plants of 'Sunmaripeach'.
5. Plants of the new *Verbena* had shorter peduncles than plants of 'Sunmaripeach'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena.*

The photograph at the top of the sheet comprises a side perspective view of a typical flowering plant of 'Sunmariapri' grown in a container.

The photograph at the bottom of the sheet is a close-up view of a typical flowering plant of 'Sunmariapri'.

DETAILED BOTANICAL DESCRIPTION

The aforementioned photographs and following observations and measurements describe plants grown during the early summer in 15-cm containers in an outdoor nursery in Higashiomi, Shiga, Japan and under cultural practices typical of commercial *Verbena* production. During the production of the plants, day temperatures averaged 23° C. and night temperatures averaged 13° C. Plants were five months old when the photographs were taken and four months old when the description was taken. In the following description color references are made to The Royal Horticultural Society Colour Chart, 2007 Edition, except where general terms of ordinary dictionary significance are used.

Botanical classification: *Verbena×hybrida* 'Sunmariapri'.

Parentage: Naturally-occurring branch mutation of a proprietary selection of *Verbena×hybrida* identified as code number 1800M, not patented.

Propagation:

*Type.*—By terminal cuttings.

*Time to initiate roots.*—About 10 to 14 days at 20° C. to 25° C.

*Time to produce a rooted young plant.*—About four weeks at 20° C. to 25° C.

*Root description.*—Fibrous; white in color.

*Rooting habit.*—Freely branching.

Plant description:

*Plant and growth habit.*—Compact, semi-upright, mounding to cascading growth habit; freely branching habit with numerous lateral branches developing per plant; pinching enhances lateral branch development; vigorous growth habit.

*Plant height.*—About 22 cm.

*Plant diameter.*—About 53 cm.

Lateral branch description:

*Length.*—About 21.8 cm.

*Diameter.*—About 2.4 mm.

*Internode length.*—About 2.3 cm.

*Strength.*—Strong.

*Aspect.*—Upright to outwardly.

*Texture.*—Densely pubescent.

*Color.*—Close to 143A.

Leaf description:

*Arrangement.*—Opposite, simple.

*Length.*—About 2.84 cm.

*Width.*—About 1.83 cm.

*Shape.*—Ovate.

*Apex.*—Obtuse.

*Base.*—Truncate.

*Margin.*—Crenate.

*Texture, upper and lower surfaces.*—Densely pubescent; coarse.

*Venation pattern.*—Pinnate; reticulate.

*Color.*—Developing leaves, upper surface: Close to 137B. Developing leaves, lower surface: Close to 137C. Fully expanded leaves, upper surface: Close to 137A; venation, close to 138B. Fully expanded leaves, lower surface: Close to 137B; venation, close to 138B.

*Petioles.*—Length: About 5 cm. Diameter: About 0.8 mm. Texture, upper and lower surfaces: Densely pubescent. Color, upper and lower surfaces: Close to 144B.

Flower description:

*Flower arrangement and flowering habit.*—Single salverform flowers arranged in hemispherical terminal racemes; flowers face mostly upright; freely flowering habit with about 24 flowers per inflorescence and about 29 inflorescences developing per plant.

*Natural flowering season.*—Early flowering habit, plants begin flowering about four weeks after planting; long flowering period, plants flower continuously from spring to late autumn in Japan.

*Flower longevity.*—Flowers last about one week on the plant; flowers not persistent.

*Fragrance.*—None detected.

*Inflorescence height.*—About 2.9 cm.

*Inflorescence diameter.*—About 5.9 cm.

*Flowers.*—Diameter: About 1.67 cm. Depth (height): About 2.64 cm. Tube length: About 1.64 cm. Tube diameter, mid-section: About 1.4 mm.

*Flower buds.*—Length: About 9.5 mm. Diameter: About 2.2 mm. Shape: Clavate. Color: Close to 38A.

*Corolla.*—Arrangement: Single whorl of five fused petals. Petal length: About 8.3 mm. Petal width: About 6.4 mm. Petal lobe shape: Cordate. Petal lobe apex: Emarginate. Petal margin: Entire. Petal texture, upper and lower surfaces: Smooth, glabrous. Color: Petal, when opening, upper surface: Close to 38A. Petal, when opening, lower surface: Close to 36D. Petal, fully opened, upper surface: Close to 38A to 38B, color gradually becoming closer to 36D and eventually, close to158C with development. Petal, fully opened, lower surface: Close to 36D. Throat: Close to between 192D and 193B. Tube: Close to 192D.

*Calyx.*—Arrangement: One single narrow calyx tube per flower with five fused sepals. Sepal length: About 1.1 cm. Sepal width: About 1 mm. Sepal shape: Lanceolate. Sepal apex: Acute. Sepal margin: Entire. Sepal texture, upper and lower surfaces: Smooth, glabrous. Sepal color, upper surface: Close to 138A. Sepal color, lower surface: Close to 138B.

*Peduncles.*—Length: About 3.69 cm. Diameter: About 1.6 mm. Strength: Strong. Aspect: Upright to outwardly. Texture: Pubescent. Color: Close to 144B.

*Reproductive organs.*—Stamens: Quantity per flower: Four. Stamen length: About 1.52 cm. Anther shape: Ellipsoidal. Anther size: About 0.9 mm by 1.2 mm. Anther color: Close to 142B. Pollen amount: Scarce. Pollen color: Close to 11D. Pistils: Quantity per flower: One. Pistil length: About 1.81 cm. Stigma shape: Bi-parted. Stigma color: Close to 145A. Style color: Close to 145C. Ovary color: Close to 145A. Fruits and seeds: Fruit and seed development have not been observed on plants of the new *Verbena*.

Garden performance: Plants of the new *Verbena* have been observed to have good garden performance and to tolerate wind, rain and temperatures ranging from about 0° C. to about 35° C.

Pathogen & pest resistance: Plants of the new *Verbena* have not been observed to be resistant to pathogens and pests common to *Verbena* plants.

It is claimed:

1. A new and distinct *Verbena* plant named 'Sunmariapri' as illustrated and described.

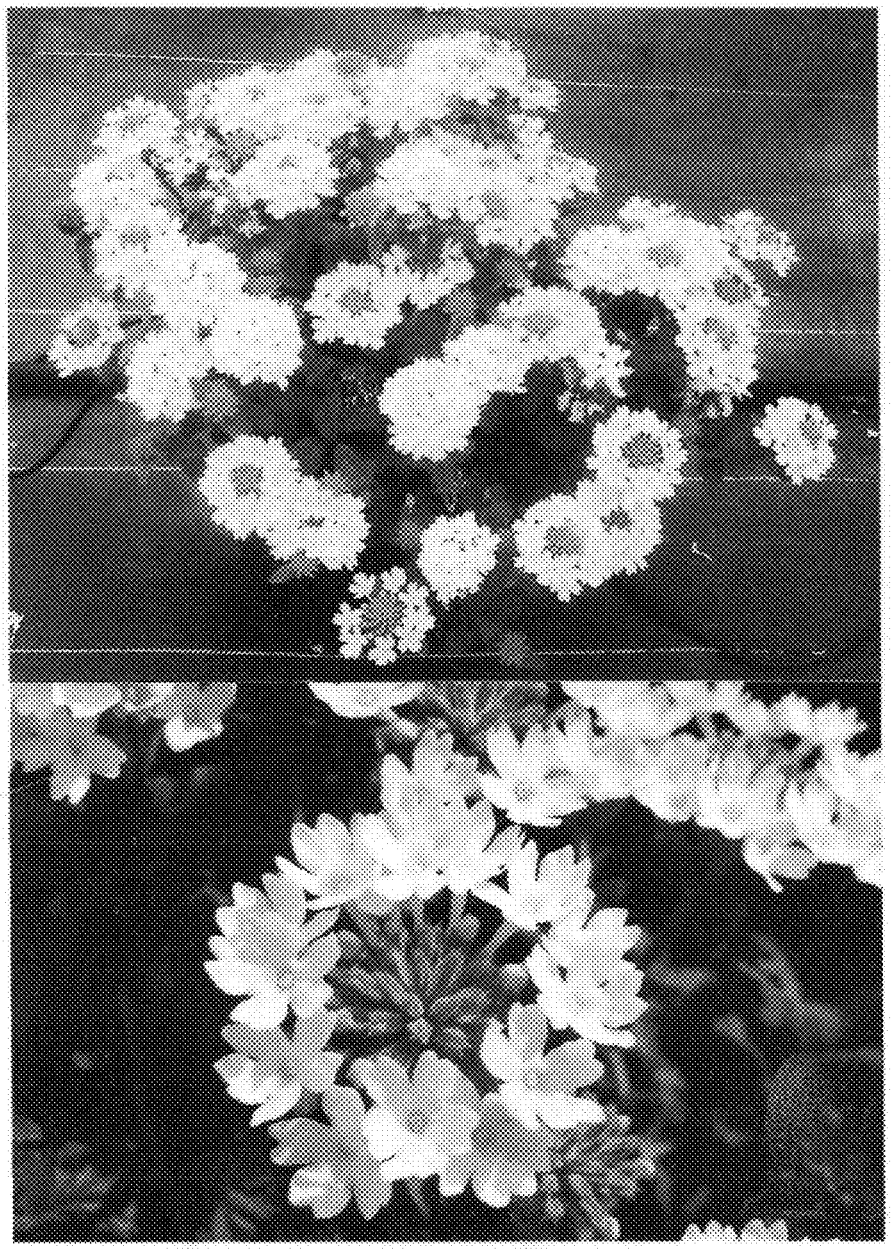

* * * * *